United States Patent [19]

Meilland

[11] Patent Number: Plant 7,666

[45] Date of Patent: Oct. 8, 1991

[54] ROSE PLANT—MEIDARKRO VARIETY

[75] Inventor: Alain A. Meilland, Antibes, France

[73] Assignee: The Conard-Pyle Company, West Grove, Pa.

[21] Appl. No.: 508,115

[22] Filed: Apr. 12, 1990

[51] Int. Cl.[5] ..... A01H 5/00

[52] U.S. Cl. ..... Plt./20

[58] Field of Search ..... Plt. 20, 21

[56] References Cited

U.S. PATENT DOCUMENTS

P.P 4,151 11/1977 Jelly ..... Plt. 20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive fully double velvet cardinal blossoms. Such blossoms are very stable and long lasting when cut and placed in a vase. The plant exhibits an erect growth habit, vigorous vegetation, and is well suited for cut flower production. Additionally, the plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Sweet Promise variety U.S. Plant Pat. No. 3,095). In the United States the Sweet Promise variety commonly is known as the Sonia variety. The male parent (i.e., the pollen parent) was the Marie DeVor variety (nonpatented in the United States). The parentage of the new variety can be summarized as follows:

[Sweet Promise variety × Marie DeVor variety].

Sweet Promise is a salmon pink Intermediate and Marie DeVor is a velvet red Grandiflora whose blossoms are substantially smaller than those of the new Hybrid Tea variety of the present invention.

The seeds resulting from the above pollination were sown and 16 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive fully double velvet cardinal blossoms which are stable and long lasting when cut and placed in a vase,
(b) exhibits an erect growth habit,
(c) exhibits a fair greenhouse forcing capability,
(d) exhibits vigorous vegetation,
(e) is partcularly suited for cut flower production, and
(f) is not particularly affected by cryptogamic diseases.

The blossom coloration is fairly well maintained during the vase life of the cut flowers. The foliage of the new variety tends to be larger and darker than that of the Sweet Promise parent, and the stems of the new variety tend to bear more thorns than the Marie DeVor parent.

The new variety well meets the needs of the horticultural industry for many usages and is particularly well suited for cut flower production. Since the new variety commonly is grown in greenhouse for cut flower production it generally does not form hips or fruit.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meidarkro variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa indicia* understock and growing in greenhouses at Cap d'Antibes, France.

FIG. 1 illustrates a specimen of a young shoot;

FIG. 4 illustrates a specimen of a floral bud at the opening of the petals;

FIG. 12 illustrates a specimen of a flowering stem;

FIG. 13 illustrates a specimen of a main branch;

FIG. 14 illustrates specimens of leaves with three leaflets—plan view—upper surface (top) and under surface (bottom);

FIG. 16 illustrates a specimen of a leaf with seven leaflets—plan view—upper surface.

DETAILED DESCRIPTION

Figures 2, 3, 5, 6, 7, 8, 9, 10, 11, 15:
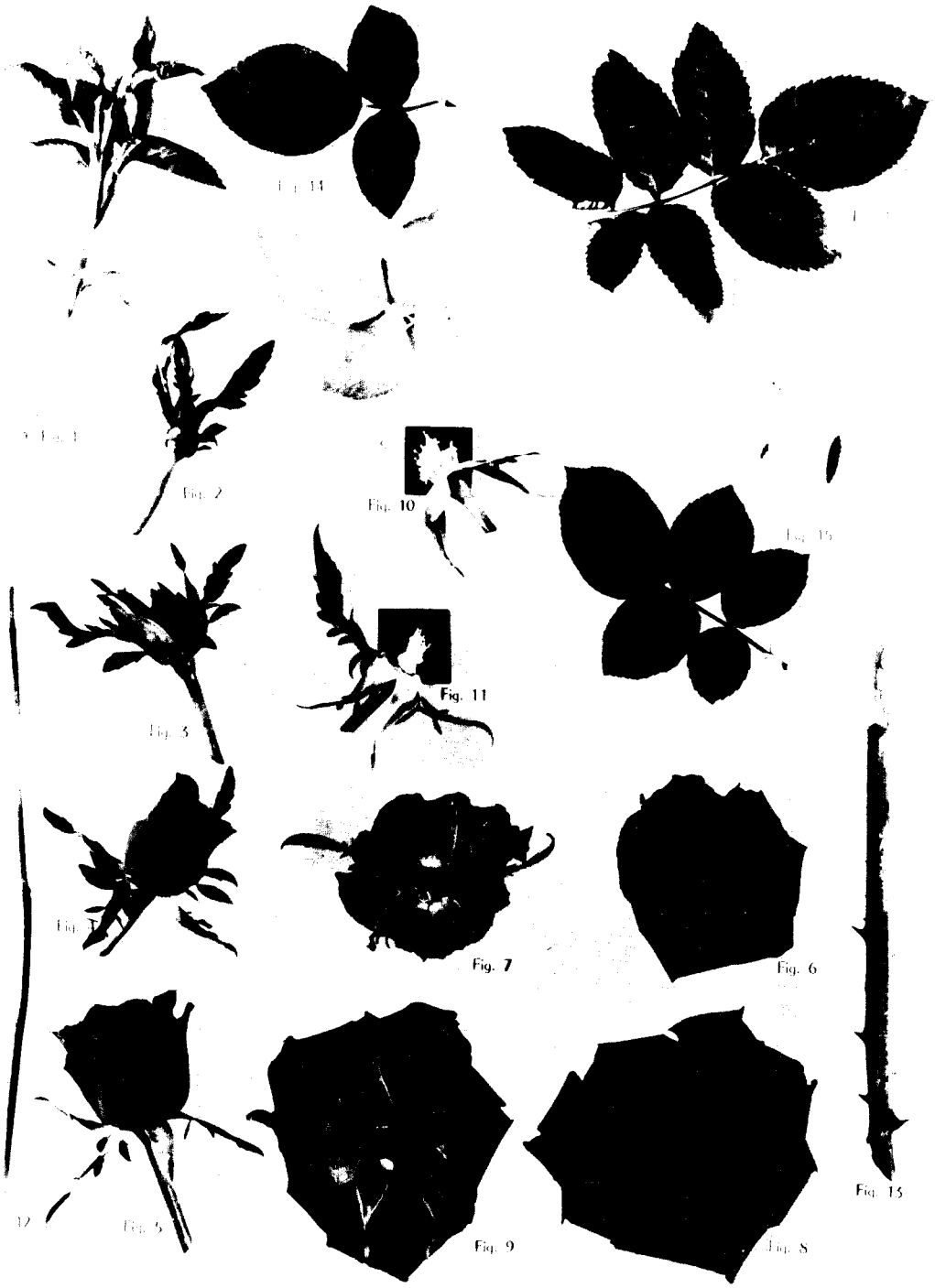
FIG. 2 illustrates a specimen of a floral bud before the opening of the sepals.
FIG. 3 illustrates a specimen of a floral bud at the opening of the sepals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 15 illustrates specimens of leaves with five leaflets—plan view—under surface (top) and upper surface (bottom)

The chart used in the identification of the colors is that of The Royal Horticultural Society (R.H.S. Colour Chart). The description is based on the observation of two year old plants made during June while budded on *Rose indicia* understock and growing in greenhouses at Cap d'Antibes, France. The coloration in common terms precedes reference to the chart.

Class: Hybrid Tea.

Plant:

*Height.*—Plants which were pruned to a height of 85 cm. produce floral stems having a length of approximately 70 to 90 cm. When grown in fields at Wasco, Calif., plants will assume an average height of approximately 1.3 m. at the end of the growing season.

*Habit.*—Erect.

Branches:

*Color.*—Young stems: medium green, Yellow-Green Group 146A, more or less stained with reddish coloration. Adult wood: medium green, Yellow-Green Group 146B.

*Thorns.*—Size: medium. Quantity: none on flowering stems and very few on adult wood. Color: pinkish-green and changing to tan mature wood.

Leaves:

*Stipules.*—Adnate, pectinate, narrow and linear.

*Petioles.*—Upper surface: striped reddish brown on young foliage and medium green on adult foliage with more or less glandular edges. Under surface: light green, and smooth.

*Leaflets.*—Number: 3, 5 (most often) and 7. Shape: elliptic, the lower leaves on the stems commonly have an incomplete first pair of leaflets, and the top leaflet commonly bears a foliar appendix. Serration: single and regular. Texture: consistent. General appearance: full, dense and semi-dull foliage. Color (young foliage): Upper surface: reddish-brown in coloration. Under surface: reddish-brown in coloration. Color (adult foliage): Upper surface: medium green, Yellow-Green Group 147B. Under surface: light green, Yellow-Green Group 148C to 148D.

Inflorescence:

*Number of flowers.*—Usually one per stem.

*Peduncle.*—Straight, rigid, smooth, light green in coloration, and bears a few pediculate glands. The length is approximately 9 to 10 cm. on average.

*Sepals.*—Upper surface: tomentose, greenish in coloration. Under surface: medium green in coloration, the outer sepals commonly have very appendiculate edges which end with a well-developed foliar appendix.

*Buds.*—Shape: conical. Length: approximately 4 cm. on average. Size: large. Color upon opening: Upper surface: dark currant velvet, Red Group 46A. Under surface: mat cardinal, Red Group 53A.

*Flower.*—Shape: cup-like and fully double. Diameter: approximately 11 cm. on average. Color (when opening begins): Upper surface: velvet currant, Red Group 46A. Under surface: dull cardinal, Red Group 53B. Color (when blooming): Upper surface: velvet cardinal, Red Group 44A. Under surface: light cardinal, Red Group 46B. Color (at end of opening): Upper surface: velvet cardinal, Red Group 44A. Under surface: light cardinal, Red Group 46B. Fragrance: none. Lasting quality: long when cut and placed in vase. Petal number: approximately 31 on average plus a few petaloids. Texture: consistent. Petal drop: very good. Stamen number: approximately 126 on average. Anthers: normal, ochre. Filaments: fuschia in coloration, of irregular heights. Pistils: approximately 83 on average. Stigmas: strawlike and located above the stamens. Styles: strawlike with fuschia tips, tomentose at the base, more or less twisted, of irregular heights. Receptacle: smooth, light green, in longitudinal section it is in the shape of a wide funnel.

Development:

*Vegetation.*—Very vigorous.

*Blooming.*—Abundant.

*Resistance to diseases.*—Good.

*Aptitude to forcing.*—Fair.

I claim:

1. A new and distinct variety of Hybrid Tea rose plant characterized by the following combination of characteristics:

(a) forms in abundance attractive fully double velvet cardinal blossoms which are stable and long lasting when cut and placed in a vase,
(b) exhibits an erect growth habit,
(c) exhibits a fair greenhouse forcing capability,
(d) exhibits vigorous vegetation,
(e) is particularly suited for cut flower production, and
(f) is not particularly affected by cryptogamic diseases, substantially as herein shown and described.

* * * * *